(12) United States Patent
Blixt et al.

(10) Patent No.: US 8,562,136 B2
(45) Date of Patent: Oct. 22, 2013

(54) VISUAL DISPLAY WITH ILLUMINATORS FOR GAZE TRACKING

(75) Inventors: Peter Blixt, Hagersten (SE); Anders Hoglund, Balsta (SE); Bengt Rehnstrom, Vasterhaninge (SE); John Elvesjö, Stockholm (SE)

(73) Assignee: Tobii Technology AB (SE)

( * ) Notice: Subject to any disclaimer, the term of this patent is extended or adjusted under 35 U.S.C. 154(b) by 0 days.

(21) Appl. No.: 13/465,245

(22) Filed: May 7, 2012
(Under 37 CFR 1.47)

(65) Prior Publication Data

US 2012/0327101 A1    Dec. 27, 2012

Related U.S. Application Data

(62) Division of application No. 12/750,967, filed on Mar. 31, 2010, now Pat. No. 8,220,926.

(60) Provisional application No. 61/165,558, filed on Apr. 1, 2009.

(30) Foreign Application Priority Data

Apr. 1, 2009    (EP) ..................................... 09157106

(51) Int. Cl.
*A61B 3/14* (2006.01)
*A61B 3/00* (2006.01)

(52) U.S. Cl.
USPC ............................ 351/210; 351/209; 351/246

(58) Field of Classification Search
USPC .............................................. 351/200–246
See application file for complete search history.

(56) References Cited

U.S. PATENT DOCUMENTS

| 4,772,885 | A | 9/1988 | Uehara et al. |
| 7,513,620 | B2 | 4/2009 | Dai et al. |
| 7,808,587 | B2 | 10/2010 | Shirasaka et al. |
| 7,963,652 | B2 * | 6/2011 | Vertegaal et al. ............. 351/205 |
| 8,220,926 | B2 * | 7/2012 | Blixt et al. ..................... 351/210 |
| 2003/0123027 | A1 | 7/2003 | Amir et al. .................... 351/209 |

(Continued)

FOREIGN PATENT DOCUMENTS

| EP | 2037352 | 8/2008 | ............. G06F 3/042 |
| WO | 2005/046465 | 5/2005 | ................ G06F 3/00 |
| WO | 2008/066460 | 6/2008 | ................ G06F 3/01 |
| WO | 2009/027773 | 3/2009 | ............. G06F 3/042 |

OTHER PUBLICATIONS

Nishino et al. "*Corneal Imaging System: Environment from Eyes*" International Journal of Computer Vision 70(1). 23-40, Apr. 1, 2006.

(Continued)

*Primary Examiner* — Mohammed Hasan
(74) *Attorney, Agent, or Firm* — Allen, Dyer, Doppelt, Milbrath & Gilchrist, P.A.

(57) ABSTRACT

A visual display characterized by hidden reference illuminators is adapted to emit invisible light for generating corneoscleral reflections on an eye watching a screen surface of the display. The tracking of such reflections and the pupil center provides input for gaze tracking. A method for equipping and an LCD with a reference illuminator are also provided. A system and method for determining a gaze point of an eye watching a visual display comprising reference illuminators are further provided. The determination of the gaze point may be based on an ellipsoidal cornea model.

20 Claims, 9 Drawing Sheets

(56) References Cited

U.S. PATENT DOCUMENTS

| | | | |
|---|---|---|---|
| 2004/0061831 A1* | 4/2004 | Aughey et al. | 351/209 |
| 2006/0239670 A1 | 10/2006 | Cleveland | 396/51 |
| 2008/0079687 A1 | 4/2008 | Cernasov | 345/102 |
| 2008/0122792 A1 | 5/2008 | Izadi et al. | 345/173 |
| 2009/0027336 A1 | 1/2009 | Lin et al. | 345/158 |
| 2009/0073142 A1 | 3/2009 | Yamashita et al. | 345/176 |

OTHER PUBLICATIONS

Guestrin, et al. "*General Theory of Remote Gaze Estimation Using the Pupil Center and Corneal Reflections*" IEEE Transactions on Biomedical Engineering, vol. 53, No. 6, Jun. 2006; pp. 1124-1133.

Wang, et al. "*The Innovative color LCD by using three color bank scrolling backlights*" SPIE vol. 7232; pp. G1-11, Feb. 12, 2009.

* cited by examiner

VISUAL DISPLAY WITH ILLUMINATORS FOR GAZE TRACKING

RELATED APPLICATION

This is a divisional patent application of U.S. patent application Ser. No. 12/750,967 filed Apr. 1, 2010, Now U.S. Pat. No. 8,220,926 B2 the entire disclosure of which is hereby incorporated herein by reference.

RELATED APPLICATIONS

This application claims the benefit of U.S. Provisional Application Ser. No. 61/165,558 filed Apr. 1, 2009, the entire contents of which are incorporated herein by reference.

FIELD OF THE INVENTION

The invention disclosed herein generally relates to visual display devices having illuminators for facilitating gaze tracking of a viewer of the display. More particularly, a visual display may be adapted to assist in gaze tracking using the pupil-center-corneal-reflection (PCCR) approach.

BACKGROUND OF THE INVENTION

In PCCR eye tracking, the gaze vector of an eye is determined on the basis of on an image of the eye when illuminated in such manner that reflections (glints) appear on the cornea. Glint positions and the pupil center position are extracted from the image using generic computer-vision methods. Methods for computing the gaze vector based on these positions are known in the art, e.g., through the teachings of E. D. Guestrin and M. Eizenmann in IEEE Transactions on Biomedical Engineering, Vol. 53, No. 6, pp. 1124-1133 (June 2006), included herein by reference.

An important application of PCCR eye-tracking technology is the task of finding the gaze point of a person watching a visual display. Since visual displays are artefacts constructed generally with the aim of providing optimal viewing conditions in terms of luminance, viewing distance and angle, image contrast etc., it might be expected that the measurement accuracy is very high in this situation, particularly when the eye tracking is performed indoors with a controlled ambient illumination.

In many practical cases, however, a considerable unreliability is introduced by the difficulty to provide illuminators that are not unsuitably distant from the expected gaze point. Indeed, the reflection created by an oblique illuminator may fall on the sclera, outside the cornea, and since the sclera has spherical shape with respect to the eye's center of rotation, this reflection is not useful for determining the orientation of the eye.

There have been attempts to place illuminators on the display screen surface. Measurements according to this approach may not always give authentic results, because each illuminator acts a visible stimulus and perturbs the natural behaviour of the person.

Other attempts include arranging illuminators on the border of the visual display, that is, outside the screen surface on which the display is adapted to create visual images. This means that the border cannot be made narrow, contrary to normal aesthetic wishes. This difficulty is accentuated if a two-dimensional array of illuminators is to be provided on each border segment, which is desirable for an accurate two-dimensional position measurement of the cornea. Combining reflections from illuminators arranged on opposing borders of the display is usually not feasible, for it is only in a narrow range of viewing angles, near the center, that reflections from both borders fall on the cornea.

Third, interlacing the visual display image with a geometrically distinct reference pattern for creating corneal reflections has been tried. Unless a display dedicated for producing both visible images and an invisible reference pattern is used, the reference pattern is generated by visible light. The interlacing may be performed intermittently during short time intervals, which are synchronised with the intervals for measuring the corneal reflection of the reference pattern. A common difficulty in implementing this approach is that the time intervals, however short, may need to occur rather frequently to achieve sufficient signal power of the reference pattern. Then, because of the time-integrating functioning of the retina, a perceptible superimposed image of the reference pattern may be produced and distract the subject.

Hence, for gaze tracking in connection with visual displays, there is a need for improved illuminators not suffering from the problems outlined above.

Two further shortcomings are inherent in many known PCCR implementations. First, the processing involved in finding the pupil center in an eye image may be problematic. For subjects having a dark iris color, particularly in the absence of a retinal reflection, the faint pupil-to-iris contrast can make the pupil boundary difficult to discern with a limited computational effort. Second, as noted in the already cited article by Guestrin and Eizenmann, the approximation of the cornea as a spherical surface is an important source of errors. Indeed, it has long been known in the art of visual optics that the cornea rather has an ellipsoidal shape, and it would be desirable to achieve improved illuminators for eye-tracking that represent a progress also with respect to these shortcomings.

SUMMARY OF THE INVENTION

It is an object of the present invention to provide a device and method for facilitating gaze tracking of a person watching a visual display.

According to a first aspect of the present invention, as defined by the independent claims, there is provided a visual display having reference illuminators adapted to generate corneo-scleral reflections (glints) on an eye watching a screen surface, adapted to display graphical information, of the visual display. The reference illuminators are adapted to emit light outside the visible spectrum, i.e., wavelengths in the range between 380 nm and 750 nm approximately. Moreover, in order that the reference illuminators themselves do not visually distract the eye, they are arranged hidden beneath the screen surface adapted to display graphical information.

Reference illuminators according to the invention can be used in gaze tracking without introducing unauthentic stimuli, for in normal operating conditions neither the illuminators nor their emitted light are visible to the human eye. The eye image, which is used for computing the gaze point, is acquired by an apparatus sensitive to, at least, light outside the visual spectrum. Advantageously, the reference illuminators are adapted to emit infrared (IR) or near-infrared light. On the one hand, the IR spectrum is adjacent to the visual spectrum, permitting use of existing imaging devices with only minor modifications and limited chromatic aberration. On the other hand, IR light is known not be harmless to the eye, unlike ultraviolet light which is also adjacent to the visible spectrum.

As a further advantage of the invention, the illuminators can be located in arbitrary positions with respect to the observed screen surface. Many of those skilled in the art of PCCR gaze tracking prefer positioning glint-generating illuminators near the center of the observed object, in order that glints falling on the sclera in certain viewing angles are avoided. Thus, unlike prior art displays having reference illuminators arranged on the border, the invention allows for optimal positioning of the reference illuminators.

Clearly, the reference illuminators beneath the screen surface must not be concealed by opaque material, such as a rear reflector layer for enhancing luminance. On the other hand, they must not obstruct the path of visible light rays propagating from beneath (i.e., towards an expected position of a viewer) which produce the graphical information visible on the screen surface. Hence, as the skilled person realises, the desirable position of the reference illuminators is beneath the source of the visible light rays for producing the graphical information, but in front of any opaque objects in the structure of the visual display.

Many available visual displays are internally organised as layers arranged parallel with the screen surface. The rear boundary of the last (i.e., deepest) layer that emits visible light and the front boundary of the first (i.e., most superficial) reflecting layer may be contiguous or separated by a small distance. If they are separated, an interstitial space—possibly containing translucent material—is created which may be advantageous in achieving an even screen luminance. It is believed that one skilled in the art, having studied and understood the present disclosure, may in such circumstances determine the most suitable depth position of the reference illuminators in this interstitial space by routine experimentation.

The invention can be embodied as visual displays of various kinds, including a liquid crystal display (LCD) and an organic light-emitting diode (LED) display. Embodiments of the invention are directed to both edge-lit LCDs and LCD with direct backlighting. In one embodiment, the liquid crystal panel is synchronised with the backlight and the reference illuminators. When a reference illuminator is active, the liquid crystal panel is 'blanked' (is maximally transmissive, and would produce white color if was lit) and the backlight is inactive. It is thereby avoided than an occasionally dark portion of the panel blocks one or more reference illuminators.

In accordance with a second aspect of the present invention, there is provided a method for equipping an LCD with a reference illuminator adapted to emit a beam of invisible light. An LCD susceptible of being equipped according to the method generally comprises the following or equivalent parts: a screen surface, adapted to display graphical information; a plurality of layers, which are translucent or at least operable to be translucent, arranged between the screen surface and essentially parallel with the screen surface; and at least one opaque layer, such as a rear reflector or a rear cover.

To arrange a reference illuminator in such LCD, a hole is provided in the opaque layer or layers. The illuminator is then mounted, by suitable fastening means, so that its beam will project perpendicularly to the screen surface—or alternatively, in the direction of an expected eye location—and concentrically with respect to the hole. The size and shape of the hole corresponds to the cross section of the beam where it crosses the hole.

In accordance with a third aspect of the present invention, there is provided a system for determining a gaze point of an eye watching a visual display according to the invention. The system comprises a camera and a processor, which may be physically separate devices or an integrated unit. The display, camera and processor may even be embodied as a single entity. The camera is adapted to acquire an image of the eye including corneo-scleral reflections of the reference illuminators provided at the visual display.

The processor is adapted to determine a gaze point using an the inverse of a mapping between a coordinate system in the object plane, which may be the screen surface or its proximity, and a coordinate system in an image plane, in which the eye is imaged. The mapping is a composition of an ellipsoidal reflection mapping (the reflection in the cornea) and a perspective projection (the imaging performed by the camera optics).

Although the mapping is a priori in regards to its structure, numerical parameters specifying the mapping need to be estimated by comparing the known geometry of the reference illuminator arrangement and the camera image of its reflection in the cornea and/or sclera. The camera parameters, which can be measured in a calibration process, determine the quantitative properties of the perspective projection. Further, the reflection mapping is partially known after calibration, during which the corneal shape of the actual eye has been fitted to an ellipsoid. (As is clear to those skilled in the art, a sphere is the special case of three axes of an ellipsoid being equal; fitting the cornea to a spherical surface may satisfy accuracy requirements in connection with some applications.)

Thus, the reflection mapping is defined up to the actual orientation and position of the cornea. The parameters encoding position and orientation are estimated by comparing the known configuration of the reference illuminators with their image in the camera. More precisely, if several reflections are available, the estimation can be based on an analysis of how length ratios and angles change under the mapping.

In a preferred embodiment of the system for determining a gaze point, the camera is provided near a lower edge of the visual display, e.g., on the frame surrounding the screen surface. Then advantageously, the eye is imaged slightly from below, whereby generally the line of sight is not hindered by protruding brow bones, thick eye-lashes and the like.

The system for determining a gaze point may be adapted to select what illuminator to use based on the actual glint position. A centrally located glint is generally preferable over one located further out, towards the sclera. In an alternative embodiment, several light sources at one time are used. Then, in principle, more information is available for use in estimation of the orientation of the cornea. As a potential drawback, however, additional reflections may create noise that deteriorates the measurement accuracy.

In accordance with a fourth aspect of the invention, there is provided a method for determining a gaze point of an eye watching a visual display. The method comprises the following actions:

the eye is illuminated by invisible light from a plurality of reference illuminators provided in an object plane;

an image of the eye, including corneo-scleral reflections of the reference illuminators, is acquired;

based on the locations of the corneo-scleral reflections in the image plane, a mapping between a coordinate system in the object plane and a coordinate system in the image plane is defined; and based on the mapping, the eye's gaze point in the object coordinate system is determined.

The mapping is composed of an ellipsoidal reflection mapping and a perspective projection, as outlined above. The ellipsoid, in which the reflection occurs according to the model, may in particular be prolate, with the optic axis of the eye as its symmetry axis; the reflection mapping can then be characterized as a prolate spherical reflection mapping. According to an advantageous embodiment of the method, the eye is illuminated using reference illuminators arranged beneath a screen surface of the visual display, the screen surface being adapted to display visible graphical information.

These and other aspects of the invention will be apparent from and elucidated with reference to the embodiments described hereinafter.

BRIEF DESCRIPTION OF THE DRAWINGS

Embodiments of the present invention will now be described with reference to the accompanying drawings, on which.

DETAILED DESCRIPTION OF EMBODIMENTS

I. Visual Display

In liquid crystal displays (LCDs), a backlight flow is passed through a liquid crystal panel capable of locally attenuating or blocking light that passes through it, wherein the pixels are the smallest sub-regions of the panel that are controllable autonomously. Such an LCD may be capable of producing color images if the backlight essentially is white (i.e., composed by a plurality of wavelengths) and colored absorption filters, corresponding to color components, are arranged in front of individual sub-pixels.

Figure 1A:
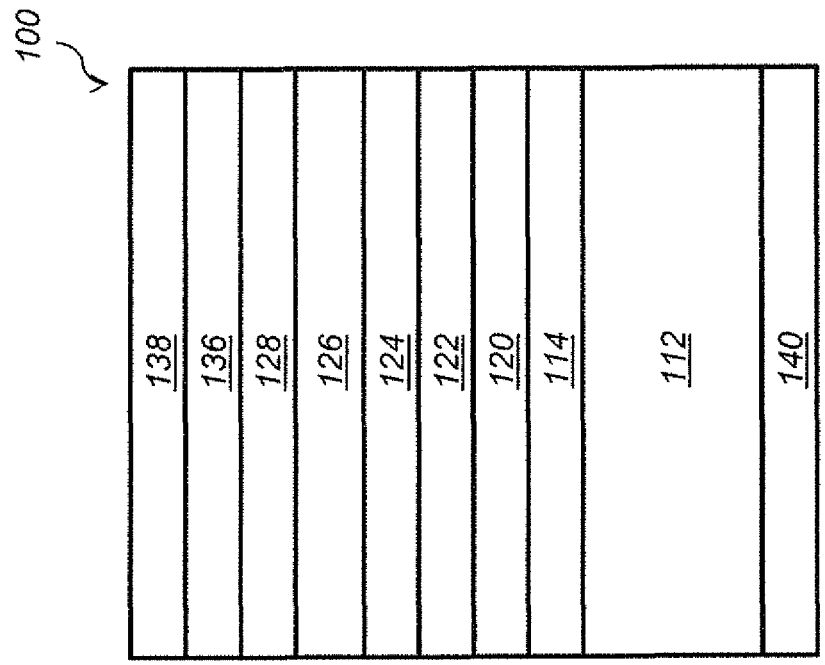
FIGS. 1a and 1b are diagrams of the layers in two exemplary LCDs.

An exemplary configuration of an LCD layer structure 100 under one pixel is shown in FIG. 1a. The top of the structure 100 faces a screen surface (not shown) of the LCD, and the bottom faces a rear cover (not shown) if such is provided; hence, light generally flows upwards in the drawing, towards a viewer (not shown). A backlight 110 layer emits the backlight flow for providing the necessary luminance of the screen surface. The light from the backlight layer 110 is passed to a diffuser 114 through a backlight cavity 112. By virtue of the distance created by the cavity 112, light cones emanating from luminous points of the backlight layer 110 are allowed to widen before the light flow is further smoothened by the diffuser 114. The next group of layers 120-138 constitute the liquid crystal panel, which is operable to pixel-wise block light, so that images are formed.

First, the incident light is polarized by a rear polarizer layer 120. The optical activity of the liquid crystal layer 126—more precisely, the extent to which it changes the polarization angle of light passing through it—can be varied by applying an electric field over the layer. A thin-film transistor (TFT) layer 122 is used to govern the amount of charge between different regions of an addressing structure 124 and a common electrode 128. The light is spectrally filtered by red 130, green 132 and blue 134 spectral filters coated on a glass plate 136, and is subsequently repolarized by the front polarizer 138.

Since the transmittance of layers 120-128 can be changed independently under each color filter 130-134, it is possible to change the apparent color point (i.e., after mixing the respective contributions from the red, green and blue sub-pixels) of the pixel. Further details on the structure and operation of LCDs may be had from a study of the article Sh. Morozumi, Active-Matrix Thin-Film Transistor Liquid-Crystal Displays, in Advances in Electronics and Electron Physics, Vol. 77 (1990), which is included in this disclosure by reference.

Figure 2:
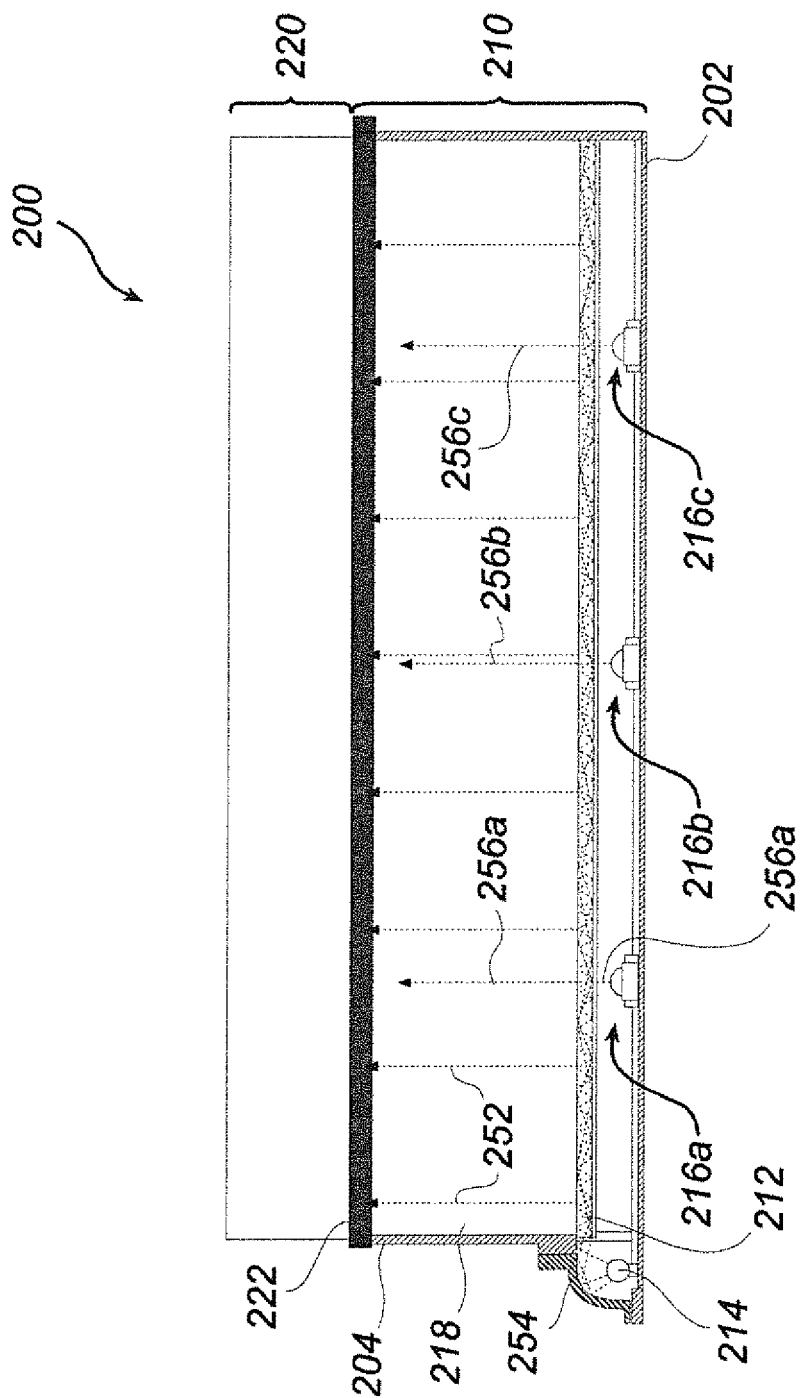
FIG. 2 is a cross-sectional view of an edge-lit LCD comprising reference illuminators according to an embodiment of the invention.

FIG. 2 is a cross section (not to scale) of an edge-lit LCD 200 provided with reference illuminators 216 according to an embodiment of the invention. The backlight is generated by section 210, which is bounded on the sides by a housing 204, on its rear side by a rear reflector 202 and is open in the forward direction (upwards in the drawing) towards an image-forming LCD panel 220. A light guide 212 is optically coupled to an edge-mounted light source 214, which may be a fluorescent tube (extending orthogonally to the plane of the drawing) or an arrangement of LEDs. In this embodiment, the light guide 212 receives light 256 at different angles of incidence, by virtue of the curved reflective surface 254 that optically connects the light source 214 to the light guide 212.

The refractive index of the light guide 212 is chosen in order that a suitable portion 252 of the light ray leaves the guide 212 at each internal reflection. Suitably, the surface of the light guide 212 is matte, to ensure that local luminance variations are not too abrupt. Light leaving the light guide 212 laterally or rearwards is recovered by being reflected back from the inside of the housing 204 or the rear reflector 202, both of which are adapted to reflect visible light. Hence, apart from absorption losses, all light 256 emitted by the light source 214 leaves the backlight section in a forwardly direction, towards the LCD panel 220, a rear diffuser 222 of which evens luminance variations out.

Reference illuminators 216 are arranged beneath the light guide 212. Rays 256 of invisible light from the reference illuminators 216 pass through the light guide 212 under small angles of incidence, and therefore undergo little change as regards their direction and intensity. Preferably, each reference illuminator 216 has a cone-shaped radiation pattern, wherein the cone subtends a solid angle of approximately $\pi$ steradians (corresponding to the cone having an apex angle of about 1.14 radians or 33 degrees of arc). The light cone may be even narrower, such as $0.8\pi$, $0.6\pi$ or $0.4\pi$ steradians.

Figure 4:
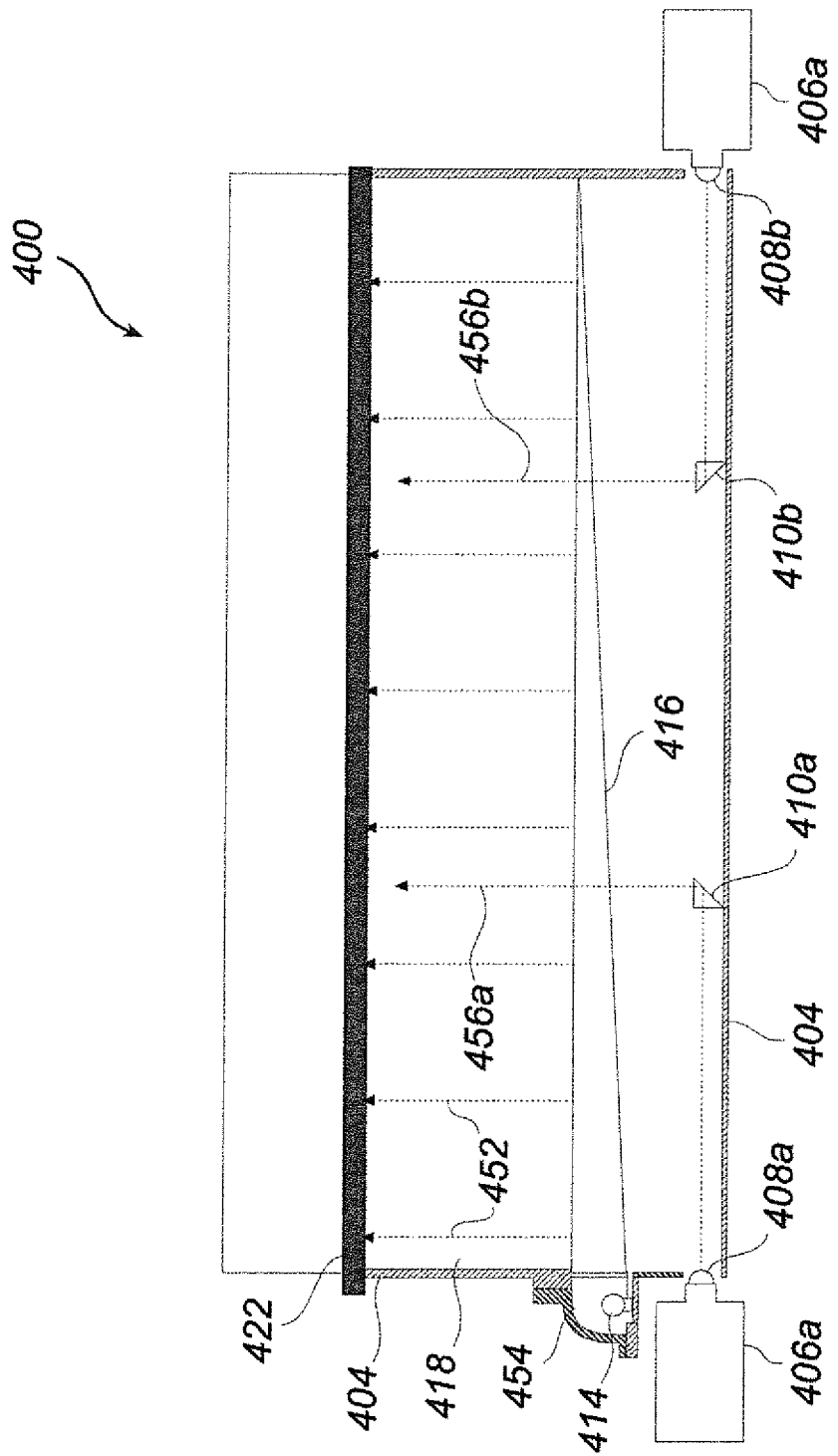
FIG. 4 is a cross-sectional view of an edge-lit LCD comprising edge-mounted reference illuminators in accordance with an embodiment of the invention.

This embodiment of the invention can be varied in accordance with various LCD backlight configurations. For example, as a light guide one may use (in combination with a suitable edge light source) a translucent sheet that causes a portion of light travelling tangentially to leave the sheet in the forwardly direction. The sheet may contain particles with a differing refractive index or may comprise a Fresnel pattern. If such translucent sheet, details of which are well known in the art and will be briefly discussed in connection with FIG. 4, is combined with a rear reflector to reflect leaking light back, then reference illuminators according to the invention are arranged in a position between the reflector and the sheet.

As another variation, the rear reflector 202 may be replaced by an absorbing element, such as a dark matte surface. Likewise, the inside of the housing 204 may be accomplished as a non-reflective surface, at least in the wavelength range of the reference illuminators 216. Although this measure will slightly decrease the energy efficiency of the LCD, it may lessen measurement noise produced by secondary rays emanating from reflections of the reference illuminators 216. From the construction disclosed above, the skilled person may extract the following principles, which are likely to facilitate adaptation of the invention to other display types:

the reference illuminators may not be arranged beneath an opaque layer;

the reference illuminators may not be arranged so superficially that they are visible to a viewer of the screen in normal conditions; and the energy efficiency of the reference illuminators can be increased by being located more superficially, so that a lesser portion of the emitted light is absorbed.

As a variation to the embodiment shown in FIG. 2, the LCD 200 may be operated in an interlaced manner. Namely, the reference illuminators may only be active in a reference mode, wherein the edge-mounted light source 214 is turned off and the liquid-crystal panel 120-138 is blanked (displays white color), at least in neighbourhoods of the reference illuminators. When not in this mode, the LCD 200 is adapted to be in the display mode, wherein the light source 214 is turned on and the liquid-crystal panel 120-138 displays graphical information. The alternation frequency, as well as the durations of the respective modes, may be determined by the skilled person by routine experimentation. The desirable result is a non-flickering image with sufficient luminance.

Figure 3:
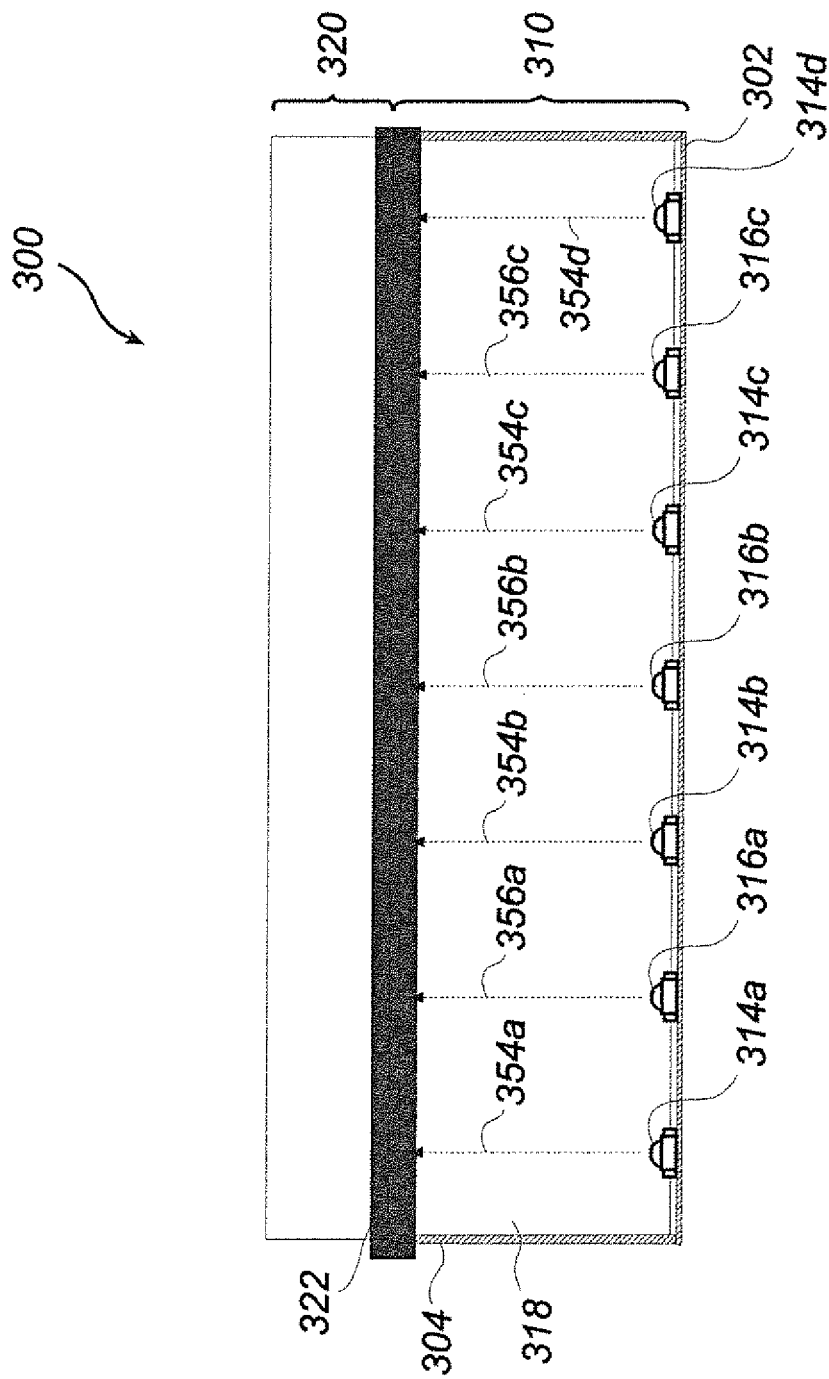
FIG. 3 is a cross-sectional view of a LCD with direct backlight, comprising reference illuminators according to an embodiment of the invention.

FIG. 3 is a cross-sectional view (not to scale) of a directly lit LCD 300, which generally consists of a backlight section 310 and an LCD panel 320. The backlight is generated by a plurality of light sources 314 (typically 100-1000 LEDs adapted to emit in the visible spectrum) arranged in a plane essentially parallel to the screen surface. To achieve an even luminance, the light sources 314 are arranged evenly over the screen surface, preferably in the shape of an array.

Light beams 354 emitted by the light sources 314 travel through a backlight cavity 318 before reaching a first layer of the LCD panel 320, namely a diffuser 322. In accordance with the invention, reference illuminators 316 (typically 1-10 infrared or near-infrared LEDs) are arranged among the light sources 314. Advantageously, reference illuminators 316 are of a similar type as the light sources 314, so that electrical connections and the like need not be specially adapted. The means for controlling the reference illuminators 316 may however be different.

Notably, if the visual display is adapted to be part of an eye tracking system in which one reference illuminator is active at a time or an automated shifting between different reference illuminators is intended, then each reference illuminator is independently controllable. It is noted that the diffuser 322 may to a certain extent blur the reference illuminators 316, just like the light sources 314 are purposefully blurred to create an even screen luminance, so that the corneo-scleral glints become less clear.

However, it has been observed empirically that the optic action of available diffusers can be accurately modelled as a scattering phenomenon, notably Rayleigh scattering, which affects longer wavelengths to a smaller extent than shorter. For this reason, the problem of blurred reference illuminators is much limited if these have a wavelength greater than that of the light sources 314. Measurements have been performed on a commercially available backlight diffuser, and the data given in TABLE 1 below were obtained.

TABLE 1

Transmittance of LCD layers, as a function of wavelength (λ)

| λ (nm) | Transmittance of TFT layer | Transmittance of TFT layer and diffuser |
|---|---|---|
| 780 | 0.12 | 0.053 |
| 830 | 0.14 | 0.064 |
| 850 | 0.15 | 0.069 |
| 910 | 0.19 | 0.088 |
| 940 | 0.20 | 0.091 |
| 970 | 0.22 | 0.100 |

Figure 10:
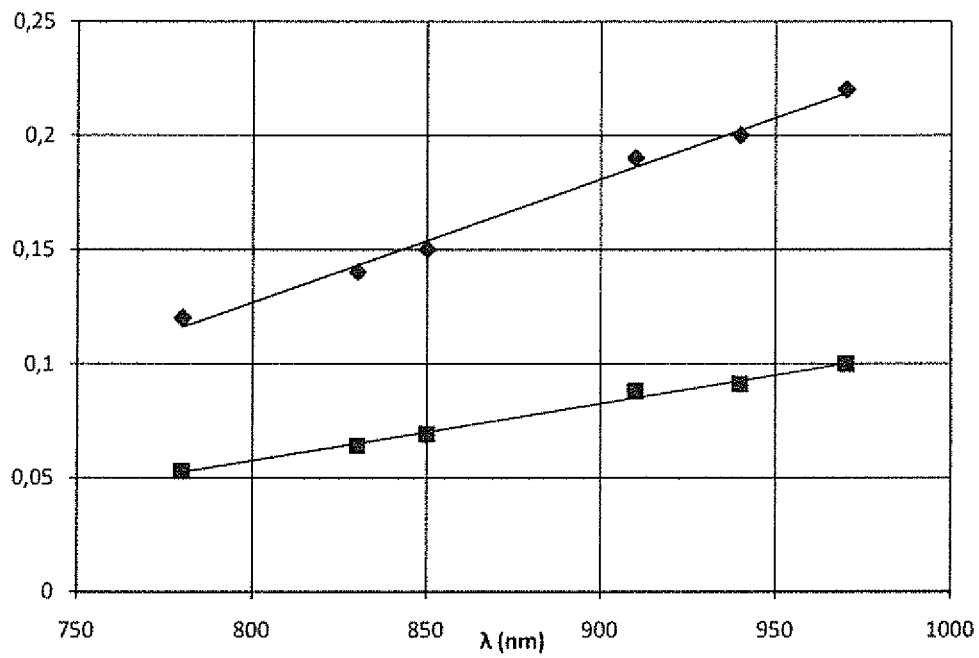
FIG. 10 is a plot of the optical transmittance of light at different wavelengths of various layers of an LCD.

The data are shown graphically in FIG. 10, wherein transmittance values of the TFT layer alone has been indicated by diamonds (◇) and those of the TFT layer in combination with a diffuser plate by squares (□). Evidently, there is no local transmittance minimum in the studied wavelength interval, and the relation between wavelength increments and transmittance increments is positive and approximately linear.

A possible physical explanation is that scattering is responsible for the attenuation at shorter wavelengths. Since scattering decreases with wavelength, transmittance increases. The transmittance of all the layers in an LCD, as experienced by an 850-nm reference illuminator arranged in accordance with the invention, has been determined empirically to be approximately 0.10 in a representative case. Clearly, the TFT layer accounts for the most important attenuation.

Figure 1B:
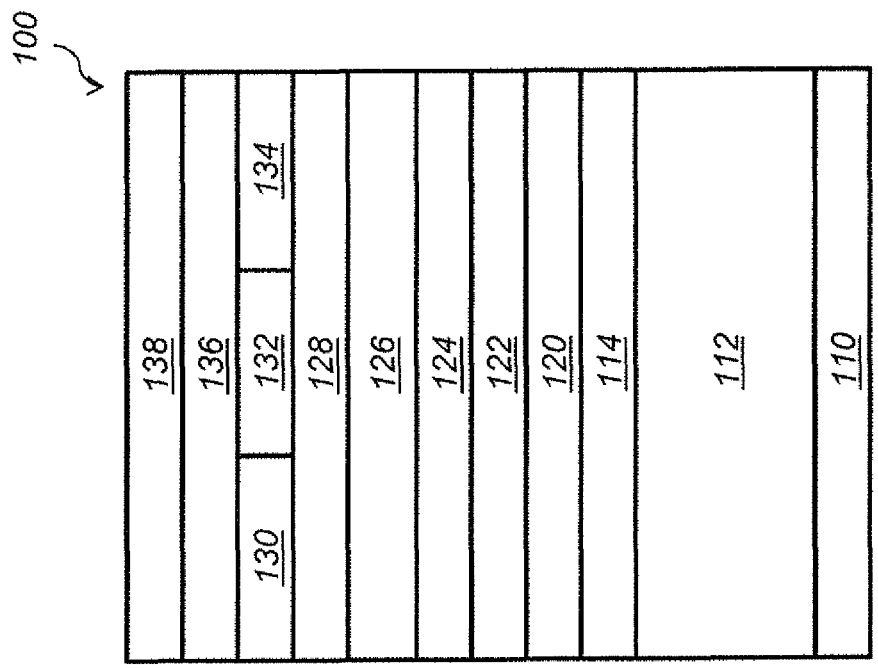

J. Ch. Wang and J. L. Lin have reported on a modified directly-lit LCD in their paper The innovative color LCD by using three color bank scrolling backlights, SPIE Photonics West (January 2009), paper 7232-15. Their modified LCD produces color images by temporal mixing, as opposed to the spatial mixing between sub-pixels of conventional color displays. The principle is illustrated in FIG. 1b, wherein, compared with FIG. 1a, the colored absorption filters 130, 132 and 134 have been deleted and the generic backlight layer 110 has been exchanged for an array 140 of colored LEDs having, say, red, green and blue color. The liquid-crystal panel 120-138 is now operated in a 'scrolling' mode, that is, it alternates cyclically between three phases:

a) red LEDs are active, liquid-crystal panel displays the red image component;

b) green LEDs are active, liquid-crystal panel displays the green image component; and c) blue LEDs are active, liquid-crystal panel displays the blue image component.

The phases need not be performed in this order. With sufficient synchronisation and suitably tuned parameters (notably the duration of each phase), the retinal image formed in the eye of a person watching such display will be perceived as a single, non-flickering color image.

How the invention can be embodied in connection with an LCD modified in accordance with Wang and Lin is illustrated with reference to FIG. 3 by assigning a new function to some of the structural elements represented therein, as per TABLE 2 below.

TABLE 2

Reference numerals of FIG. 3 when showing a modified LCD

| | |
|---|---|
| 314a | red LED |
| 316a | green LED |
| 314b | blue LED |
| 316b | reference illuminator |
| 314c | red LED |
| 316c | green LED |
| 314d | blue LED |
| 320 | cyclically alternating liquid-crystal panel not containing colored absorption filters |

The figure merely shows a portion of the visual display unit. The total number of red, green and blue LEDs is larger than the number of reference illuminators by at least one order of magnitude. It is noted that the reference illuminators are preferably near-infrared or infrared LEDs. The reference illuminators may be active in phase a) (red) of the cycle, which gives the least wavelength difference, or may be active in the entire cycle. More preferably, however, a four-phase cycle may be devised, as follows:

a') as phase a) above;
b') as phase b) above;
c') as phase c) above; and
d') reference illuminator(s) active, liquid-crystal panel maximally transmissive ('blanked').

An advantage of activating the reference illuminator in a separate phase (which may lead to a lower mean luminance of the display) is that the risk is removed of having the active reference illuminator obscured by a dark portion of the image. If (near)infrared light is used as reference light, the reference illuminators may be LEDs of mainly red color having an emission spectrum that extends also into the (near)infrared spectrum; they may then be active in the 'red' phase so that the extra phase d') is dispensed with.

FIG. 4 is a cross-sectional view (not to scale) of an LCD 400 comprising reference illuminators 406 in accordance with the invention. In relation to the LCD 200 shown in FIG. 2, the present embodiment exhibits some similar features. Backlight is supplied by a light source 414 in a lateral cavity and is conducted by a light guide 416 through a backlight cavity 418 as vertical rays 452, evenly distributed over the extent of the display, which eventually reach a rear diffuser 422, from which the rays are further fed to a liquid-crystal panel above. In contrast to the light guide 216 of FIG. 2, the present light guide 416 is wedge-shaped to ensure an even luminance. Its top side may comprise a pattern of small prisms extending orthogonally to the plane of the drawing, as detailed in U.S. Pat. No. 5,797,668. There is no drawback in using a wedge-shaped light guide 416 in association with an LCD of the type shown in FIG. 2.

In order to achieve a thinner LCD, the reference illuminators 406 are edge-mounted. The light emitted by each reference illuminator 406 is focused into a beam by lens 408 and is internally reflected into the transverse (forwardly) direction in a prism 410. The triangular cross section of the prism 410 has angles of 45 and 90 degrees, the smaller sides facing the reference illuminator and the liquid-crystal panel, respectively.

To achieve total internal reflection, a prism 410 has a refractive index of at least 1.414. It may be advantageous, e.g., for mechanical reasons, to arrange the prisms 410 embedded in a sheet of resin or a similar material suitable as a light guide; then, it is the ratio of the prism's refractive index and that of the resin which should not be below 1.414. In an alternative embodiment, the layer comprising the light source 414 and light guide 416 may be located beneath the layer of the reference illuminators 406 and the prisms 410.

Indeed, although the prisms act as reflectors for lateral light rays, the most part of light impinging from below on the hypotenuse will be transmitted through the prism, however with a small change of direction which may affect the luminance of the screen locally. It is noted that the arrangement of edge-mounted reference illuminators 406 and prisms 410 discussed in this paragraph can also be applied to LCDs having direct backlight and to organic LED displays.

Figure 5:
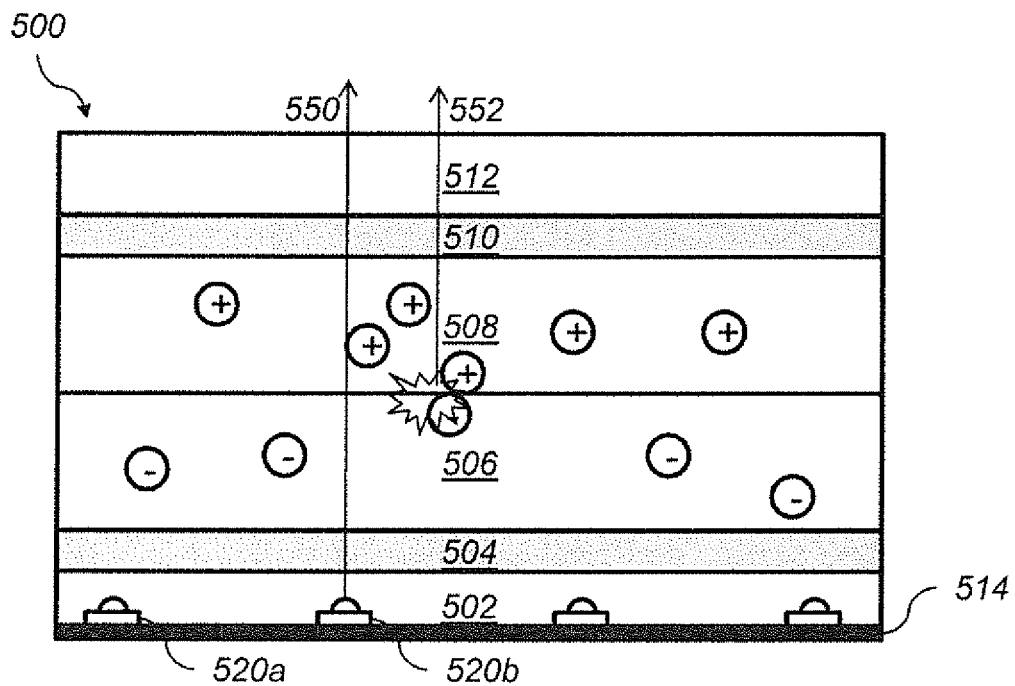
FIG. 5 is a cross-sectional view of an organic LED display comprising reference illuminators according to an embodiment of the invention.

FIG. 5 is a diagrammatic cross-sectional view of an organic LED display 500, which comprises a cathode 504, an emissive layer 506, a conductive layer 508, an anode 510 and a transparent layer 512 for protecting the layers beneath and for supplying mechanical stiffness. According to a widely embraced theory, light emission in an organic LED display is caused by electron-hole recombination.

By applying a potential difference between the cathode 504 and the anode 508, such recombination is stimulated locally but not very far outside the region of the potential difference. Thus, graphical information can be displayed as a luminous image on the organic LED display screen. In a layer 502 beneath the cathode 504, a plurality of reference illuminators 520 are arranged, similarly to, e.g., the display 200 shown in FIG. 2. The surface 514 may be reflective if a brighter display image is desirable, or absorbent if an even luminance is preferred; the latter option will entail less reflections of the reference illuminators 520, which may be harmful to accuracy, as already discussed.

Figure 7:
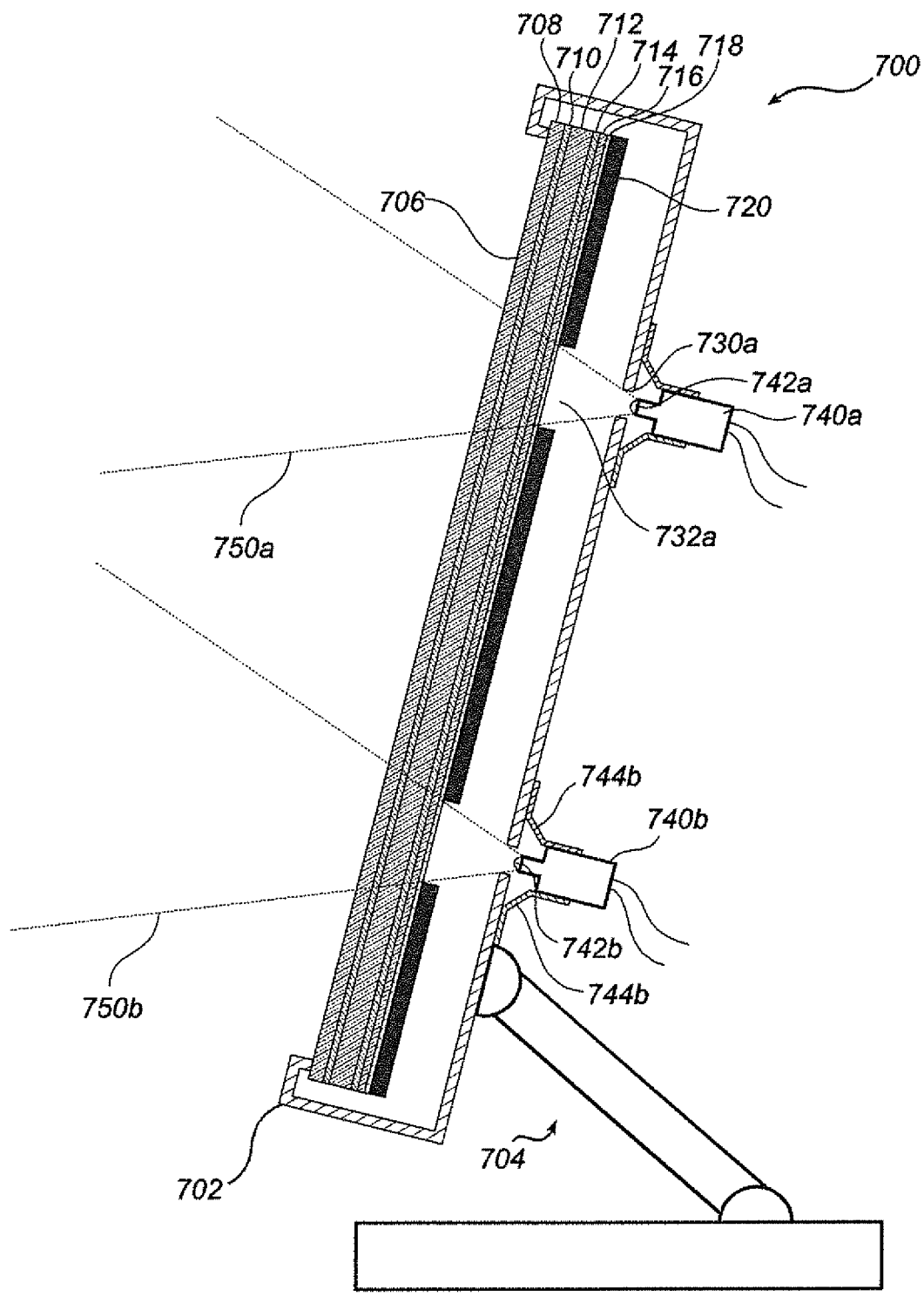
FIG. 7 is a cross-sectional view of an LCD having undergone equipping by reference illuminators according to an embodiment of the invention.

FIG. 7 is a cross-sectional view of an LCD 700 having been equipped with reference illuminators according to the inventive method. The LCD 700 generally consists of a housing 702 carried by a support 704 adapted to rest on an essentially horizontal surface. The LCD 700 is adapted to produce a luminous graphical image on a screen surface 706, beneath which translucent layers 708-718 are arranged, such as a diffuser, color filters, a thin film transistor, a liquid crystal layer and a backlight layer.

An opaque layer is arranged beneath the translucent layers 708-718. To enhance the brightness of the screen surface 706, the layer 720 may be reflective. Alternatively, the layer 720 is an absorber plate, whereby a more even luminance is achieved. In accordance with the invention, reference illuminators 740 are provided on the rear side of the LCD 700. The reference illuminators 740 are supported in a position essentially orthogonal to the screen surface 706 by fastening means 744 attaching them to the rear portion of the housing 702. The shape of a light cone 750 emanating from each reference illuminator 740 is determined, in part, by a lens 742 provided in front of the illuminator 740. The limits of the light cone indicated in FIG. 7 are approximate and may be understood, e.g., as the angle at which the intensity has dropped to half of the maximal value. Holes 730, 732 are provided in the rear portion of the housing 702 and in the reflector 720, respectively.

The shape and size of the holes 730, 732 correspond to the shape and size of the light cones 750. It is emphasized that the drawing is not to scale, but for clarity the thickness of layers 708-720 has been exaggerated as has the distance between layer 720 and the rear portion of the housing 702; notably, to accommodate the light 750 cones, the width of the holes 730, 732 is disproportionate.

II. Gaze Tracking System

Figure 6:
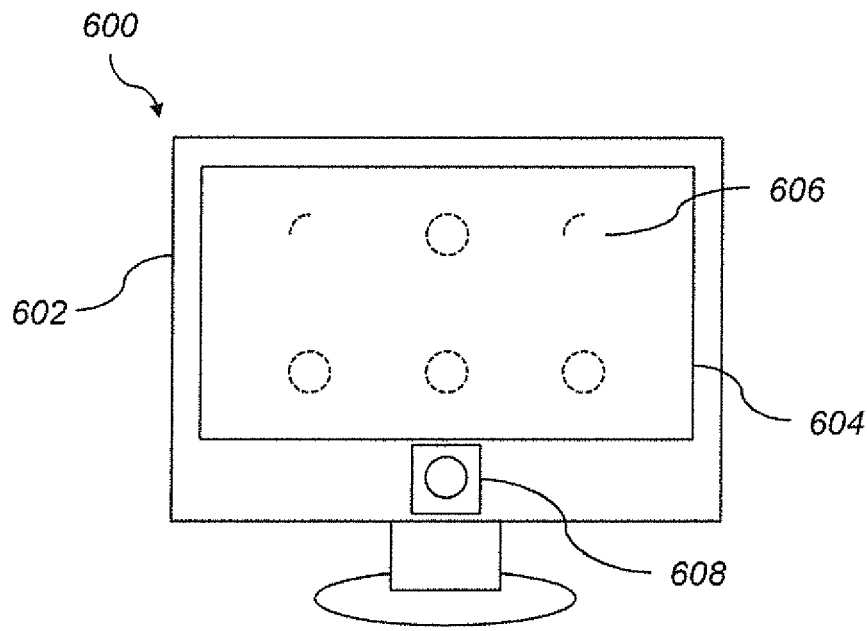
FIG. 6 shows a system for gaze tracking according to an embodiment of the invention.

FIG. 6 shows an integrated system 600 for gaze tracking in accordance with an embodiment of the present invention. A visual display 602 comprises a screen surface 604 adapted to produce a luminous representation of graphical information. Reference illuminators 606 adapted to emit invisible light (preferably infrared or near-infrared light) are arranged beneath the screen surface 604 in such manner that they are invisible in normal conditions.

The system further comprises a camera 608 for imaging an eye of a person watching the screen surface 604. The camera is arranged at the lower portion of the visual display 602, so that the line of sight from the camera to each eye is likely to pass below the brow bone and to the side of the nose. Locations of both the pupil center and glints produced by the reference illuminators 606, the camera 608 is sensitive to both visible light and the light emitted by the reference illuminators 606.

The reference illuminators 606 and the camera 608 are operated in a coordinated manner by a processor (not shown), which is also adapted to compute and output a gaze point of the person based on the data collected by the system 600. The operation may follow the method described in section IV below. The gaze point computation may be based on a spherical or ellipsoidal cornea model, details of which are given below. As a particular example of coordinated operation of the system 600, the choice of active reference illuminator(s) may be reassessed repeatedly. For instance, the active illuminator may be selected with the aim of obtaining a glint that is centered with respect to the pupil.

In an alternative embodiment, the system 600 may comprise one or more additional sources of invisible (e.g., infrared) light arranged off the optical axis of the camera 608. More particularly, such additional light sources may be arranged on the border of the visual display 602, suitably to the left and/or right of the screen surface 604. As opposed to the reference illuminators 606, the additional light sources provide an evenly distributed intensity rather than concentrated light spots. This facilitates imaging of the eye by increasing the overall illumination of the eye.

There is an advantage in using other light sources than the reference illuminators for this, since it may sometimes be impossible to achieve a sufficient overall illumination by means of the reference illuminators 606 without saturating the light sensor at the glint locations. By arranging the additional light source far from the optical axis of the sensor, e.g., on the border of the visual display 602, there is a greater probability that the reflection image of this light source falls outside the iris. It is noted that if additional invisible illumination is provided, it may not be required that the camera 608 be sensitive to visible light.

In yet another embodiment of the system 600, a bright-pupil light source is provided in proximity of the camera 608 and coaxially therewith. Such bright-pupil light source may have annular shape and may be arranged around the camera 608. This enables tracking of the eye in both its bright-pupil and dark-pupil condition, which increases the likelihood of being able to choose an illuminator that provides optimal image quality.

III. PCCR Gaze Tracking Using an Aspherical Cornea Model

Figure 9:
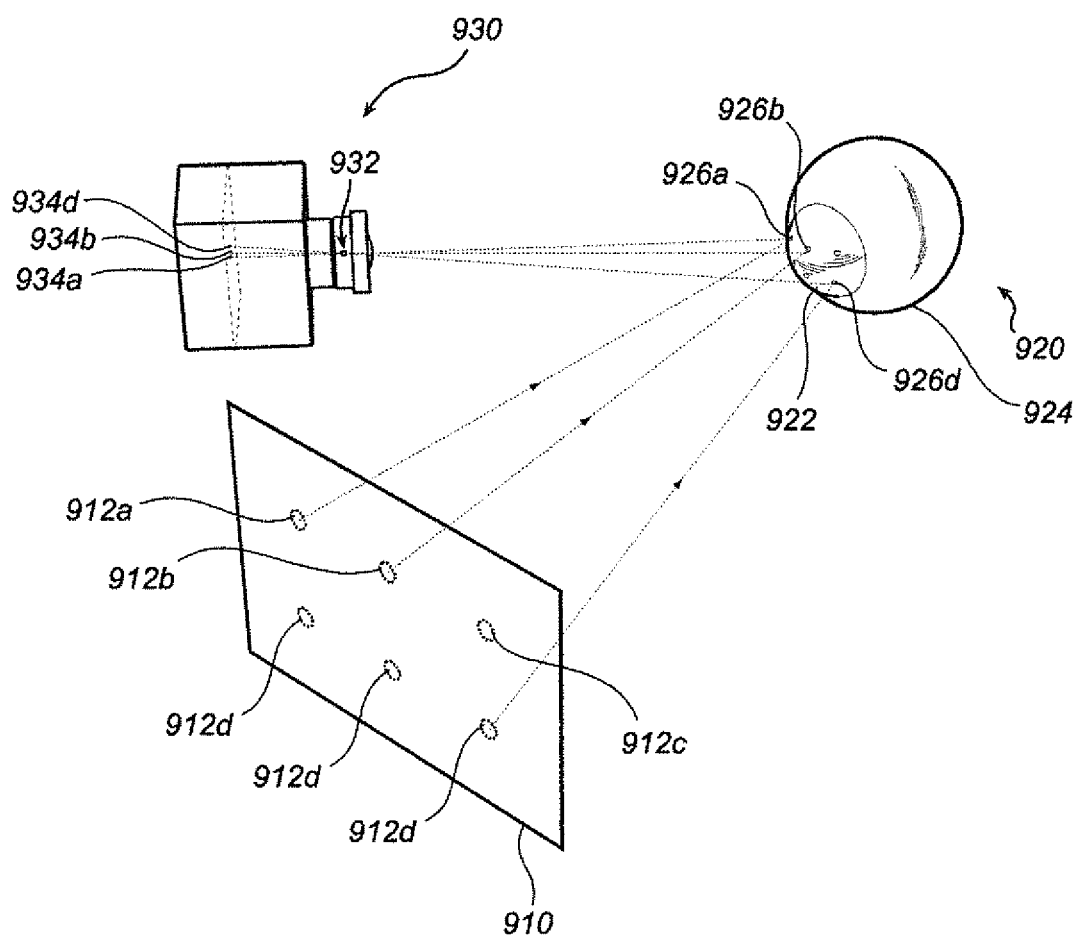
FIG. 9 is a diagrammatic perspective drawing showing an array of reference illuminators, their corneo-scleral reflection and a camera device adapted to image the eye with the reflection.

Gaze tracking using an aspherical cornea model, more particularly an ellipsoidal cornea model, will now be outlined. FIG. 9 diagrammatically depicts the experimental situation. Reference illuminators 912, each of which is independently activable, are provided in an object plane 910. The illuminators 912 are imaged as corneal reflections 926 in the cornea 922 or sclera 924 of a person's eye 920. A camera 930, which is preferably a digital imaging device, images the corneal reflections 926 as image points 934.

In a simplified model, as shown on the drawing, the imaging of the camera 930 is determined by a (rear) nodal point 932 and an image plane. For clarity, light rays are indicated from reference illuminators 912a, 912b and 912d only. The compound imaging process of the cornea 922 and the camera 930, which maps each reference illuminator 912 to an image point 934, can be expressed by the following mathematical relationship:

$$X'=[\text{Proj}\circ\text{Refl}_{T(E)}](X),$$

where

Proj is a perspective projection (which in homogeneous coordinates is a linear mapping) known through camera calibration;

E is an ellipsoid representing the corneal surface, known through personal calibration of the test subject while focusing sample points;

T is a rigid transformation which reflects the actual position and orientation of the ellipsoid;

X is a coordinate vector for an illuminator known through the predetermined illuminator arrangement; and X' is a coordinate vector for the camera image of the same illuminator.

The reflection map $\text{Refl}_{T(E)}$ (which is determined by the assumptions of rectilinear propagation of light and of equality between angles of incidence and reflection; in computer-graphics terminology it is an 'environment map') depends parametrically on T(E) which, in turn, is a function of the actual position and orientation T of the cornea. When T(E) is found, such that $$\text{Proj}^{-1}(X')=\text{Refl}_{T(E)}(X)$$

holds true (this equation is equivalent to the previous one), the position and orientation of the eye are known, and the gaze vector can be determined in a straightforward manner. The parameters specifying the mappings Proj and $\text{Refl}_{T(E)}$ can be estimated by considering pairs of known object and image points (X,X'), preferably the reference illuminators and their images under reflection in the cornea. Once the mappings are known, it is possible to find counterparts of object points in the image and vice versa; particularly, the location of the pupil center can be mapped to the image to provide an approximate gaze point.

Figure 8:
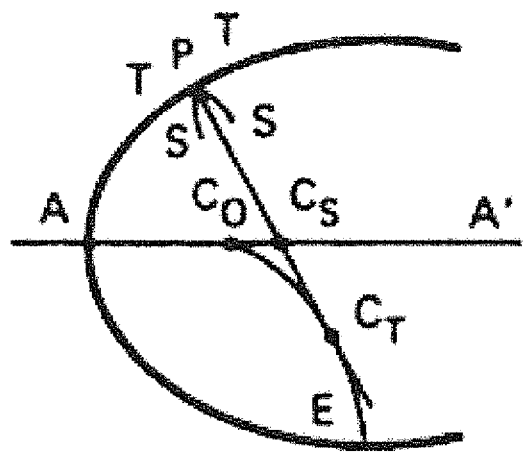
FIG. 8 is a diagrammatic cross-sectional view of the cornea.

A procedure of solving the gaze-detection problem will now be outlined; one of its advantages over gaze detection via a complete estimation of the mappings Proj and $\text{Refl}_{T(E)}$ is that sufficient information for finding the gaze-point may be obtained with fewer computations and less input data. The ellipsoid E used to model the cornea is more precisely given as a surface of revolution, with respect to the x axis, of the curve $$y^2 = 2r_0 x - px^2 \Leftrightarrow \left(\frac{x-r_0/p}{r_0/p}\right)^2 + \left(\frac{y}{r_0/\sqrt{p}}\right)^2 = 1,$$

where p<1 (the ellipsoid is prolate), x is the dorso-ventral coordinate and y is the vertical coordinate. An ellipsoid having this shape is shown in FIG. 8, wherein the line AA' represents the x axis and the y direction is vertical on the drawing. In a three-dimensional description, if a lateral coordinate z is included, E is defined by $$\left(\frac{x-r_0/p}{r_0/p}\right)^2 + \left(\frac{y}{r_0/\sqrt{p}}\right)^2 + \left(\frac{z}{r_0/\sqrt{p}}\right)^2 = 1.$$

The arc SPS in FIG. 8 represents the sagittal radius of curvature, which is given by $$r_S(y) = \sqrt{r_D^2 + (1-p)y^2},$$

where y is the height coordinate of point P. The tangential radius of curvature, as measured on the arc TPT in the plane of the drawing, is defined as $$r_T(y) = \frac{r_S(y)^3}{r_0^2}.$$

Points $C_S$ and $C_T$ are the respective centers of sagittal and tangential curvature at P. Because E is a surface of revolution, A:(0,0) is an umbilical point, at which both radii of curvature are equal to the minimal radius $r_D$. The described model is valid in the corneal portion of the eye, whereas the sclera has an approximately spherical shape. Typical values of the minimal radius and the eccentricity are $r_D=7.8$ mm and $p=0.7$, but vary between individual corneae. To achieve optimal accuracy, these constants may be determined for each test subject in a calibration step prior to the gaze tracking. The calibration step may also include determining the distance from the pupil center to the corresponding center $C_D$ of corneal curvature and the angular deviation between the visual and optic axes of the eye. It is noted that the spherical model is obtained as a special case by setting $p=1$ in the formulas above; as an immediate consequence hereof, the sagittal and tangential radii are equal.

The calculations may be carried out along the lines of the already cited article by Guestrin and Eizenmann, however with certain modifications to account for the aspherical cornea model. Following Guestrin and Eizenmann, the locus of a reference illuminator 912 is denoted by L, the nodal point 932 of the camera is denoted by O and the image 934 of the corneal reflection is denoted by U.

Because each point P≠A on the cornea has two different radii of curvature in the ellipsoidal model, the article's co-planarity assumption of vectors $\overrightarrow{LO}, \overrightarrow{OU}, \overrightarrow{OC_D}$, by which notably each line of equation 15 follows, is no longer valid. In the case of an ellipsoidal cornea model, separate equations are obtained for the tangential and sagittal components of the vectors. Separating $\overrightarrow{OU}, \overrightarrow{LO}$ in sagittal and tangential components by orthogonal projection, as per $$\overrightarrow{OU} = \vec{v}_S + \vec{v}_T,$$

$$\overrightarrow{LO} = \vec{w}_S + \vec{w}_T,$$

the following groups of co-planar vectors are obtained: $\overrightarrow{C_S P}$, $\vec{v}_S, \vec{w}_S$ and $\overrightarrow{C_T P}, \vec{v}_T, \vec{w}_T$. The calculations can then be continued in a manner similar to that disclosed in the article.

Empirically the use of an ellipsoidal cornea model leads to a significant increase in accuracy. It has even been observed that pupil-center tracking is in some cases not necessary as a supplement to glint tracking, as practised hitherto in the art.

Indeed, tracking of the cornea—apprehended as an ellipsoidal, rotationally asymmetric surface—provides sufficient information (apart from calibration data such as the angular difference between the optic axis and the visual axis) that the orientation of the eye can be determined.

Likewise, the process of calibrating certain parameters, notably the minimal radius of curvature and the eccentricity, can be simplified in so far as the test subject is not required to fix his or her eyes on training points. Such improvement of the calibration process is dependent on the correctness of the assumption that the optic axis of the eye coincides with the symmetry axis AA'. Further improvements may be achieved by using a compound light pattern or a time-varying light pattern for generating corneo-scleral glints.

IV. Method for Selecting a Combination of a Camera and Reference Illuminator

Figure 11:
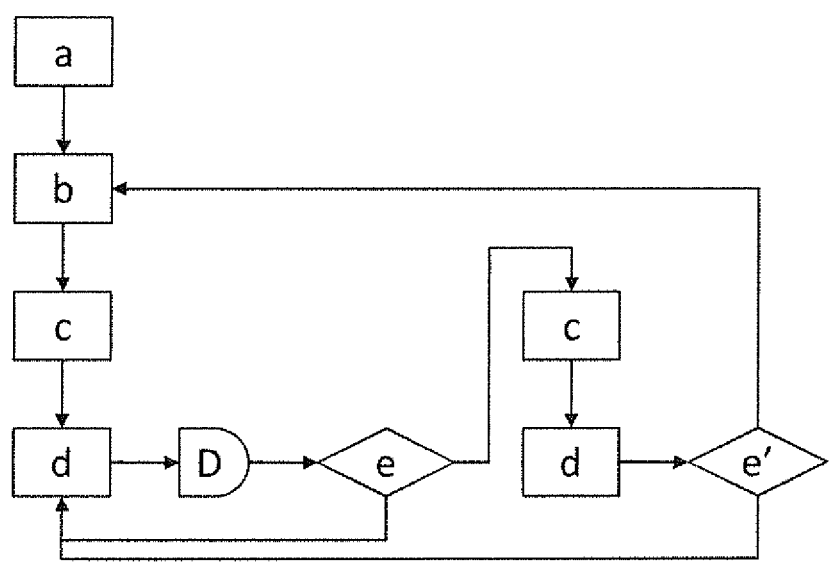
FIG. 11 is a flowchart of a method for selecting a combination of a camera and a reference illuminator.

With reference to FIG. 11, a preferred embodiment of a method for selecting a combination of an active camera and an active reference illuminator will be described. The selection is made from a plurality of reference illuminators adapted to illuminate at least one eye and a plurality of cameras adapted to image the eye or eyes with the aim of selecting that combination which provides the most suitable conditions for gaze tracking of the eye(s).

In step a) of the method, an image quality metric is defined. The image quality metric may be based on the quality factors indicated in TABLE 3 below.

TABLE 3

| Image quality factors | |
|---|---|
| NbrPupils | The number of pupils detected by the camera. Two detected pupils are preferred to one or none. |
| GazeDetNoise | If the test subject fixates a number of visible points in a calibration process, then parameters can be set to such values that the expected divergence from the true point locations is zero. The gaze-detection noise after this process can be expressed as a statistical measure (such as variance, standard deviation, maximal value etc.) of the divergence. A lower gaze-detection noise is preferred. |
| PupilContrast | The difference in luminance of a region of the pupil and a region of the iris. Preferably, the regions are located centrally in the pupil and the iris, respectively, and the luminance values are averaged over the regions. A greater pupil contrast is preferred. |
| IrisGradient | Off-axis regions in a camera's field of view may have a lower (effective) resolution than central regions. The magnitude of the gradient at the pupil-iris boundary is taken as a measure of the resolution. A greater magnitude of the gradient is preferred. |
| Obstacles | The pupil-iris boundary may be obscured by the presence of obstacles, such as eyelashes, non-transparent parts of eye glasses, reflections from eye-glass lenses, glints, eyebrows, nose and the like. It is noted that the most centric glint may lie on the pupil-iris boundary and be detrimental to the pupil finding; in such circumstances, it may be better to use the illuminator that gives the next most centric glint. The absence of obstacles is preferred. |
| SNR | A signal-to-noise ratio can be defined by taking PupilContrast (see above) as a measure of the signal intensity and the standard |

TABLE 3-continued

Image quality factors deviation at the center of the pupil, which is a normally a monochrome region, as a measure of the noise. A higher signal-to-noise ratio is preferred.

Out of these quality factors, the inventors deem NbrPupils, GazeDetNoise and PupilContrast to be the most important, whereas IrisGradient, Obstacles and SNR may be used as additional factors. The image quality factors may be combined into a total quality metric as per:
Image Quality—

$$a_1 \text{NbrPupils} + a_2 \text{GazeDetNoise} + a_3 \text{PupilContrast} + a_4 \text{Iris Gradient} + a_5 \text{Obsacles} + a_6 \text{SNR}$$

where coefficients $\alpha_1, \alpha_2, \ldots, \alpha_6$ are constants of appropriate signs. For instance, $\alpha_1$ and $\alpha_2$ should be of opposite signs, considering the preferred values of the quantities. Since the image quality metric is only used for establishing the relative quality of two images, there is no real need for an absolute calibration of the sub-metric. However, the relative weighting between sub-metrics, as reflected by the absolute values of the coefficients, should be chosen with some care to fit the requirements of the application.

The possible combinations of a camera and an illuminator fall into two groups: combinations of two coaxial components and combinations of two non-coaxial components. The combinations of coaxial components are adapted to image the eye(s) in the bright-pupil mode (a retinal retro-reflection complements the iris image), whereas the combinations of non-coaxial components are adapted to image in the dark-pupil mode (a corneo-scleral reflection complements the iris image). Step a) is followed by step b), in which either the bright-pupil or the dark-pupil imaging mode is selected. To this end, at least one image of the eye in the dark-pupil mode and at least one in the bright-pupil mode are acquired.

The comparison is more accurate if the at least two images are acquired closely in time, which also makes the selection process swifter. To maximise both these benefits, the images are acquired simultaneously if possible (that is, if only one bright-pupil image is taken) in this embodiment. Preferably, the images are acquired simultaneously. The image quality metric is evaluated for these images, and the imaging mode is selected in accordance with the highest value of the metric. If more than one image has been acquired in each mode, then the imaging mode of the image having the globally maximal quality metric is selected.

Upon completion of step b), the method proceeds to step c), wherein an active camera is selected. The image quality metric is evaluated for images acquired using combinations according to the selected imaging mode. Possibly, some images which were used in step b) may be used again. The winning quality metric value determines which camera is selected. In this step, just like in step b), the images for which the image quality factor is assessed may be acquired while the device is in an evaluation mode.

It remains to select, in step d), an active reference illuminator to be used in combination with the selected active camera. An advantageous way of finding the most suitable reference illuminator is as follows: using an initially selected reference illuminator the corneo-scleral reflection is retrieved; the deviation from the pupil center of the reflection is established; it is determined whether there is an alternative reference illuminator which has such position in relation to the initially selected illuminator (is located in a direction opposite the deviation) that a more centric corneo-scleral reflection can be achieved; if such alternative reference illuminator is available, it is selected and the centricity of the corneo-scleral glint is reassessed; if no improvement to the centricity is achieved using the alternative reference illuminator, reversion to the initially selected reference illuminator takes place. This procedure may be refined by taking into account the magnitude of the reflection's deviation from the pupil center; for instance, a relatively small deviation may not motivate use of an alternative reference illuminator.

On completion of step d), a combination of an active reference illuminator and an active camera has been selected. The centricity of the corneo-scleral reflection (step d)) is reassessed regularly, and this may provoke a decision to switch to another reference illuminator. To avoid too frequent reassessment of the centricity, a delay D of suitable duration (which the skilled person should be able to determine by routine experimentation) is provided between repetitions of step d). The delay causes an intermittent repetition of step d). Choosing a longer delay D eases the computational load, but deteriorates the accuracy of the eye tracker.

It is also possible to provide a delay D with adaptive duration, which reflects empirically observed human eye-movement patterns, such as saccadic movements. To maintain a high image quality, the image quality metric is evaluated for the selected combination, in step e), at regular intervals (such as after every completion of step d) or after every $2^{th}$, $5^{th}$, $10^{th}$ or $20^{th}$ completion). If the image quality is greater than or equal to a predetermined level, then the intermittent repetition of step d) is resumed.

If however the image quality metric is below the predetermined level although updating of the reference illuminator selection (step d)) has been effected, then the camera selection is revised by repeating steps c) and d). Immediately after such repetition, in step e'), the image quality metric is evaluated again. If the image quality metric is still below the predetermined level, then the selection of imaging mode is revised by repeating steps b), c) and d); otherwise, the method resumes the intermittent repetition of step d).

Figure 12:
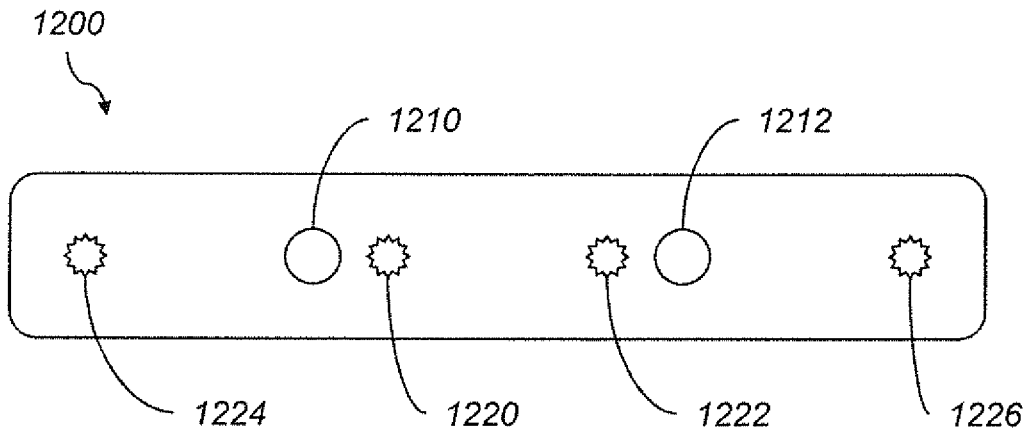
FIG. 12 shows a combined camera and illuminator arrangement.
Figure 13:
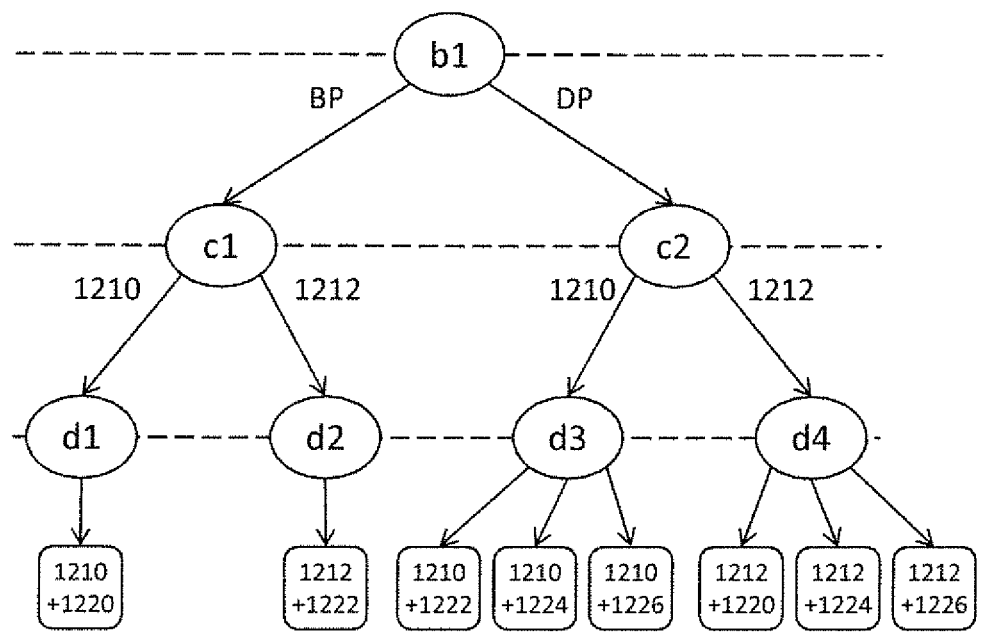
FIG. 13 is an illustration of a decision tree associated with the method for selecting a combination of a camera and a reference illuminator when applied to the combined camera and illuminator arrangement of FIG. 12.

With reference to FIG. 13, an application of the described method to the arrangement 1200 shown in FIG. 12 will now be outlined. The arrangement 1200 comprises first and second cameras 1210, 1212 and first, second, third and fourth reference illuminators 1220, 1222, 1224 and 1226. The combination of camera 1210 and illuminator 1220 is coaxial, as is the combination of camera 1212 and illuminator 1222. The other six combinations are non-coaxial.

The decisions taken during execution of the method are illustrated in the form of a tree in FIG. 13. Nodes b1, c1, c2, d1, d2, d3 and d4 symbolise decision points; an arrow symbolises a decision to select an imaging mode (on the top level), a camera (on the middle level) or an illuminator (on the lowest level); and the leaves symbolise a complete combination of an active camera and an illuminator, as indicated.

Assuming an image quality metric has been defined the first decision point b1 is whether to use the bright-pupil (BP) or dark-pupil (DP) imaging mode. If the bright-pupil mode is chosen, the method moves to decision point c1, at which the most suitable of the first camera 1210 and the second camera 1212 is selected.

No more decision is taken if the first camera 1210 is selected, for only the first illuminator 1220 is coaxial with the first camera 1210, and likewise, a selection of the second camera 1212 inevitably implies that the combination with the second illuminator 1222 will be used. Hence, decision points d1 and d2 are trivial. If instead the dark-pupil mode is selected (at decision point 101), each choice of an active camera (at decision point c2) leads to a choice of three possible reference illuminators (at each of decision points d3 and d4). When the method has reached one of the leaves in the decision tree, the initial selection of a camera-illuminator combination is complete.

The selection is updated by climbing one level up in the tree. As noted, the selection of a reference illuminator is trivial in the case of bright-pupil imaging, but at decision point d3 for instance, there is a choice between the second, third and fourth illuminators 1222, 1224, 1226. The second illuminator 1222 is likely to give the most centric corneal reflection for tracking a central gaze direction, whereas the third and fourth illuminators 1224, 1226 are probably suitable for lateral gaze directions.

The switching may be performed by a simple control mechanism. If evaluation of the image quality metric reveals that updating of the active illuminator selection cannot provide sufficient image quality, the middle decision level is resumed (backwards along the arrows of the decision tree) and possibly the top level as well, should the image quality not have improved sufficiently.

V. Closing Remarks

While the invention has been illustrated and described in detail in the drawings and foregoing description, such illustration and description are to be considered illustrative or exemplary and not restrictive; the invention is not limited to the disclosed embodiments. For example, the method of equipping a visual display with reference illuminators for gaze tracking may be performed with respect to other visual displays than those mentioned herein, such as a plasma-discharge panel, once the principles of the method have been studied and correctly understood. The placement of the reference illuminators in relation to translucent and opaque elements of the display is a notable example of such principles.

Other variations to the disclosed embodiments can be understood and effectuated by those skilled in the art in practicing the claimed invention, from a study of the drawings, the disclosure, and the appended claims. In the claims, the word 'comprising' does not exclude other elements or steps, and the indefinite article 'a' or 'an' does not exclude a plurality.

A single processor or other unit may fulfil the functions of several items received in the claims. The mere fact that certain measures are recited in mutually different dependent claims does not indicate that a combination of these measured cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A visual display comprising:
   a screen surface;
   a plurality of reference illuminators adjacent to and arranged beneath said screen surface and adapted to emit invisible light on an eye watching said screen surface;
   said screen surface adapted to display graphical information based on said plurality of reference illuminators; and
   a plurality of layers beneath said screen surface and essentially parallel therewith, wherein any layer being arranged between said plurality of reference illuminators and said screen surface is operable to be translucent.

2. The visual display according to claim 1, wherein said plurality of reference illuminators are adapted to emit infrared or near-infrared light.

3. The visual display according to claim 1, wherein a light cone of each reference illuminator is essentially normal to said screen surface and subtends a solid angle of at most $\pi$ steradians.

4. The visual display according to claim 1, wherein said plurality of reference illuminators is arranged in a two-dimensional array, with the array being parallel to said screen surface.

5. The visual display according to claim 1, wherein said visual display comprises an organic light-emitting diode display comprising a translucent anode layer, a conductive layer, an emissive layer and a translucent cathode layer, beneath which layers said plurality of reference illuminators are arranged.

6. The visual display according to claim 1, wherein said plurality of reference illuminators is adapted to illuminate an eye watching the visual display, with the eye being subject to gaze tracking.

7. A visual display comprising:
   a screen surface;
   a plurality of reference illuminators adjacent to and arranged beneath said screen surface and adapted to emit invisible light on an eye watching said screen surface;
   said screen surface adapted to display graphical information based on said plurality of reference illuminators; and
   a liquid crystal display comprising a light guide, which is optically coupled to an edge-mounted backlight illuminator, and a rear reflector layer, between which said plurality of reference illuminators is arranged.

8. The visual display according to claim 7, wherein said plurality of reference illuminators are adapted to emit infrared or near-infrared light.

9. The visual display according to claim 7, wherein a light cone of each reference illuminator is essentially normal to said screen surface and subtends a solid angle of at most $\pi$ steradians.

10. The visual display according to claim 7, wherein said plurality of reference illuminators is arranged in a two-dimensional array, with the array being parallel to said screen surface.

11. The visual display according to claim 7, further comprising a liquid crystal panel with variable transmittance, said visual display being alternately operable in:
    a display mode, wherein at least one backlight illuminator is active; and
    a reference mode, wherein said plurality of reference illuminators is active, all backlight illuminators for emitting visible light are inactive, and said liquid crystal panel has maximum transmittance.

12. The visual display according to claim 7, wherein said visual display comprises an organic light-emitting diode display comprising a translucent anode layer, a conductive layer, an emissive layer and a translucent cathode layer, beneath which layers said plurality of reference illuminators are arranged.

13. The visual display according to claim 7, wherein said plurality of reference illuminators is adapted to illuminate an eye watching the visual display, with the eye being subject to gaze tracking.

14. A visual display comprising:
    a screen surface;

a plurality of reference illuminators adjacent to and arranged beneath said screen surface and adapted to emit invisible light on an eye watching said screen surface;

said screen surface adapted to display graphical information based on said plurality of reference illuminators; and a liquid crystal display comprising a plurality of direct backlight illuminators, and wherein a subset of said plurality of backlight illuminators is at least one reference illuminator.

15. The visual display according to claim 14, wherein said plurality of reference illuminators are adapted to emit infrared or near-infrared light.

16. The visual display according to claim 14, wherein a light cone of each reference illuminator is essentially normal to said screen surface and subtends a solid angle of at most $\pi$ steradians.

17. The visual display according to claim 14, wherein said plurality of reference illuminators is arranged in a two-dimensional array, with the array being parallel to said screen surface.

18. The visual display according to claim 14, said visual display comprises a liquid crystal display comprising a plurality of direct backlight illuminators, and wherein a subset of said plurality of backlight illuminators is at least one reference illuminator.

19. The visual display according to claim 14, wherein said visual display comprises an organic light-emitting diode display comprising a translucent anode layer, a conductive layer, an emissive layer and a translucent cathode layer, beneath which layers said plurality of reference illuminators are arranged.

20. The visual display according to claim 14, wherein said plurality of reference illuminators is adapted to illuminate an eye watching the visual display, with the eye being subject to gaze tracking.

* * * * *

UNITED STATES PATENT AND TRADEMARK OFFICE
CERTIFICATE OF CORRECTION

Page 1 of 2

PATENT NO. : 8,562,136 B2
APPLICATION NO. : 13/465245
DATED : October 22, 2013
INVENTOR(S) : Blixt et al.

It is certified that error appears in the above-identified patent and that said Letters Patent is hereby corrected as shown below:

In the Drawings:   Delete: "Fig 6"

Insert: New Figure

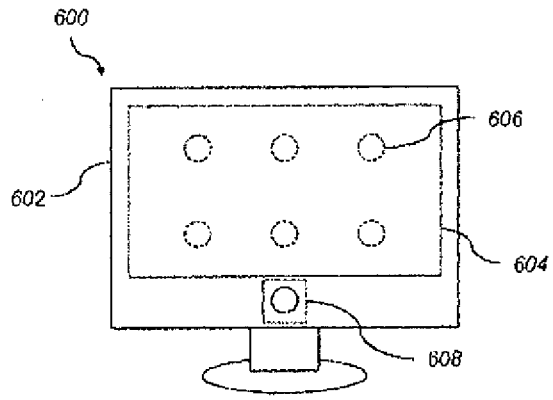

Fig. 6

In the Specification:

Column 13, Line 11,

Delete: "$r_s(y) = \sqrt{D^z + (1-p)y^z}$"

Insert: -- $r_s(y) = \sqrt{r_0^2 + (1-p)y^2}$ --

Signed and Sealed this
Eleventh Day of March, 2014

Michelle K. Lee
*Deputy Director of the United States Patent and Trademark Office*

CERTIFICATE OF CORRECTION (continued)
U.S. Pat. No. 8,562,136 B2

Column 13, Line 25,

Delete: "$r_D$"

Insert: -- $r_0$ --

Column 13, Line 28,

Delete: "$r_D =$"

Insert: -- $r_0 =$ --